United States Patent
Unger

(10) Patent No.: US 8,009,290 B2
(45) Date of Patent: Aug. 30, 2011

(54) COMPACT, LOW COST PARTICLE SENSOR

(76) Inventor: Roger L. Unger, Riverside, CA (US)

( * ) Notice: Subject to any disclaimer, the term of this patent is extended or adjusted under 35 U.S.C. 154(b) by 414 days.

(21) Appl. No.: 12/152,157

(22) Filed: May 12, 2008

(65) Prior Publication Data
US 2008/0278725 A1    Nov. 13, 2008

Related U.S. Application Data

(60) Provisional application No. 60/928,870, filed on May 12, 2007.

(51) Int. Cl.
*G01N 15/02* (2006.01)
(52) U.S. Cl. ........................................... 356/336
(58) Field of Classification Search .................... 356/336
See application file for complete search history.

(56) References Cited

U.S. PATENT DOCUMENTS

| | | | |
|---|---|---|---|
| 3,819,269 A * | 6/1974 | Duvall et al. | 356/36 |
| 4,783,599 A * | 11/1988 | Borden | 250/574 |
| 5,085,500 A | 2/1992 | Blesener | |
| 5,534,999 A * | 7/1996 | Koshizuka et al. | 356/338 |
| 5,870,190 A | 2/1999 | Unger | |
| 6,087,947 A * | 7/2000 | Hamburger et al. | 340/627 |
| 7,088,447 B1 * | 8/2006 | Bates et al. | 356/338 |
| 7,499,809 B2 * | 3/2009 | Nagura et al. | 702/29 |
| 2007/0229825 A1 | 10/2007 | Bates | |

* cited by examiner

*Primary Examiner* — Roy Punnoose

(57) ABSTRACT

A compact, low cost particle sensor utilizing a photodetector (31) which directly collects light scattered by particles (33) entrained in a fluid traversing a beam of light (32). The beam of light (32) is aligned such that it is in close proximity to the photo detector (31). The beam of light (32) is typically provided by a laser and associated focusing/collimating optics. The beam of light (32) intersects a portion of the fluid flow permitting a low pressure drop system and fluid flow generated by a low cost, low pressure device such as an axial fan (50).

18 Claims, 5 Drawing Sheets

COMPACT, LOW COST PARTICLE SENSOR

CROSS-REFERENCE TO RELATED APPLICATIONS

This application claims the benefit of provisional patent application Ser. No. 60/928,870 filed May 12, 2007 by the present inventor.

FEDERALLY SPONSORED RESEARCH

Not applicable

SEQUENCE LISTING OR PROGRAM

Not applicable

BACKGROUND

1. Field of Invention

This invention relates generally to systems that use light scattering techniques for the detection of particles in a fluid (e.g. liquid or gas), which systems are generally referred to in the art as particle sensors or particle counters.

2. Prior Art

Typically, a particle counter works by drawing a sample of air through a beam of light and detecting the light scattered off the particles entrained in the air flow. These particles scatter light in proportion to their size, composition, shape and other physical properties. Lenses, mirrors, or other light collection techniques are used to increase the portion of the scattered light which is focused onto a photoelectric device (hereinafter referred to as a photodetector). The photodetector converts this scattered light into an electrical signal. This electrical signal is typically a pulse whose amplitude is related to the amount of scattered light reaching the photodetector and whose duration is typically related to the transit time of the particle through the beam of light. Thus, from the photodetector output and associated circuitry information about the number and size of particles in a sampled volume of air can be determined.

At the present time particle counters typically cost several thousand dollars or more. Particle counters typically contain a number of expensive components or assemblies. Typically, a blower or pump is used to generate the necessary vacuum to draw the fluid flow through a sensor assembly/chamber. The sensor assembly is typically sealed except for an inlet and exhaust opening. The inlet typically has a "nozzle" or "inlet jet" which may be a machined or formed component through which the air to be sampled passes before entering the beam of light. As particle counters typically assume the total flow of air through the instrument is being sampled for particles, care must be taken in the alignment of the nozzle over the beam of light so that all air leaving the nozzle passes through the beam. The sensor will also typically contain collection optics to gather a large percentage of the light scattered off particles passing through the beam. These can consist of expensive components such as mirrors or lenses. In addition, particle counters typically use pressure sensors and/or mass flow sensors to determine the volumetric flow through the beam of light. The above components add significant cost to a particle counter.

There are many applications in which monitoring the concentration of airborne particles would be useful, such as testing indoor air quality, but a cost of several thousand dollars is a deterrent. Therefore, a need exists for a light scattering device which eliminates many of the above expensive components to provide low cost particle monitoring.

SUMMARY

The invention is an improvement in a light scattering particle sensor or optical particle counter. In accordance with one embodiment, the cross-sectional area of the flow passage through the sensor is larger than the area of the beam of light which it intersects. Thus, only a portion of the air flow is illuminated by the beam of light and only a portion of the air flow is sampled for particles. Also in the improvement, the beam of light passes in close proximity to a photodetector such that a sufficiently large percentage of the light scattered off the particles will directly strike the photodetectors as to enable particle detection without the need for a light collection system utilizing mirrors, lenses, or other light collection techniques.

The large flow passage through the sensor allows the sensor to operate at very low vacuums of less than 0.2 inches of H2O (1 inch of H2O, or water, is defined as a differential pressure of 248.84 pascals at 60 degrees Fahrenheit and a vacuum of 1 inch of H2O is a differential pressure of 248.84 pascals from ambient pressure at 60 degrees Fahrenheit). It further allows loose tolerances on the sealing of the sensor because minor leaks will not appreciably affect the flow rate through the sensor. In contrast, current particle sensors typically contain a block with an inlet and exit, but otherwise tightly sealed, referred to as a "flow cell", "sensor chamber", "detector housing", "sensor assembly", or other such name. The approach of this invention allows this block to be eliminated and the entire enclosure for the particle counter to be made of two plastic pieces injection molded to standard tolerances. Operation at low vacuum also permits the use of a low cost axial fan or blower to generate the air flow. The large flow passage also permits the elimination of a nozzle or inlet jet which typically require precise alignment to the beam of light.

In another embodiment of the invention the need to measure the flow via a pressure and/or flow sensor is eliminated by measuring the pulse width of the photo detector output to determine the transit time of the particles through the beam of light and calculate the flow rate.

In another embodiment of the invention a light baffle is placed between the beam of light and the photodetector to improve the particle size resolution.

In another embodiment of the invention a lens is placed between the beam of light and the photodetector to improve the particle size resolution.

Other details of the invention are set forth in the following detailed description and in the drawings.

DETAILED DESCRIPTION OF THE INVENTION

Figure 1:
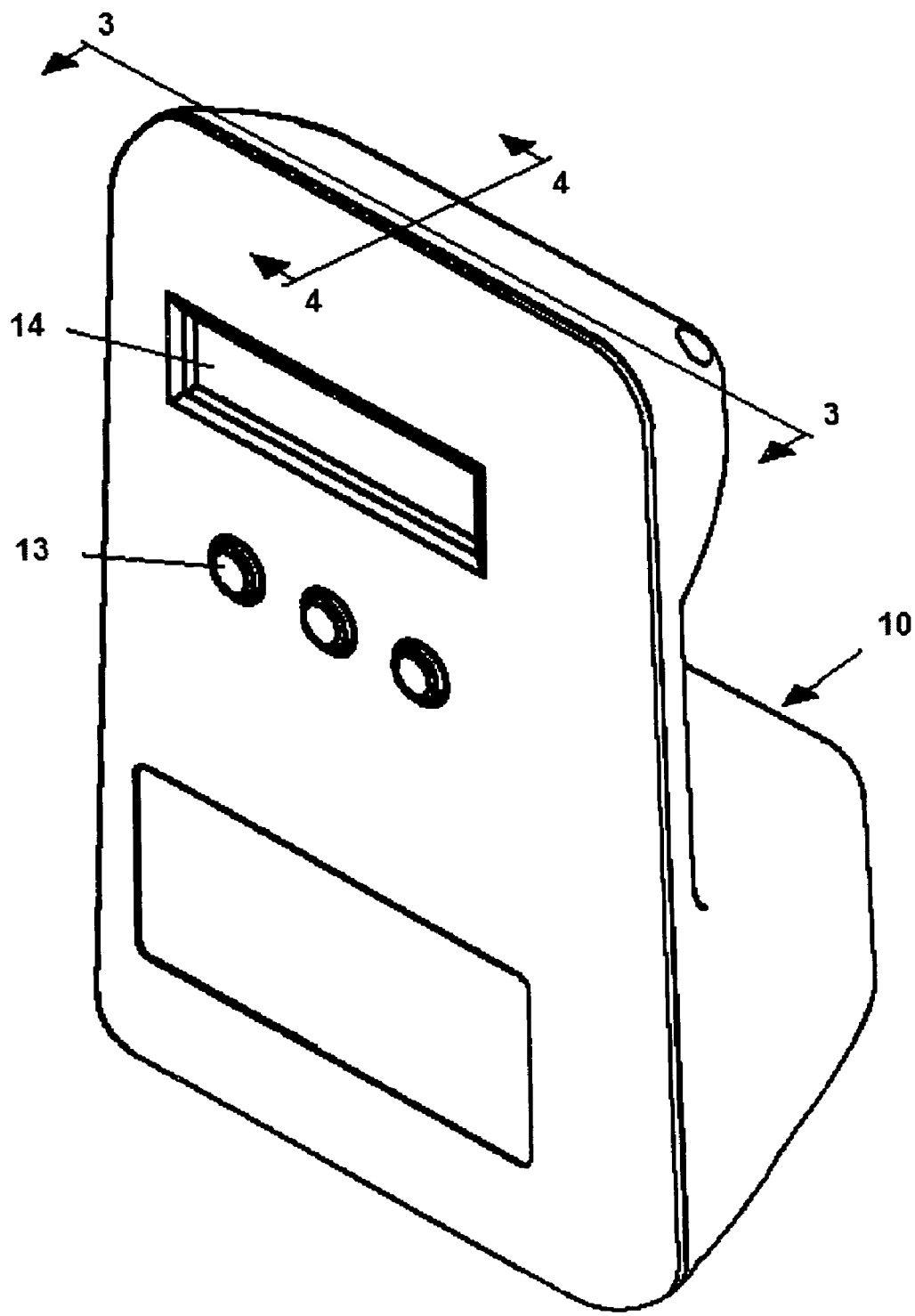
FIG. 1 is a perspective drawing of a particle sensor constructed according to the principles of the present invention.
Figure 2:
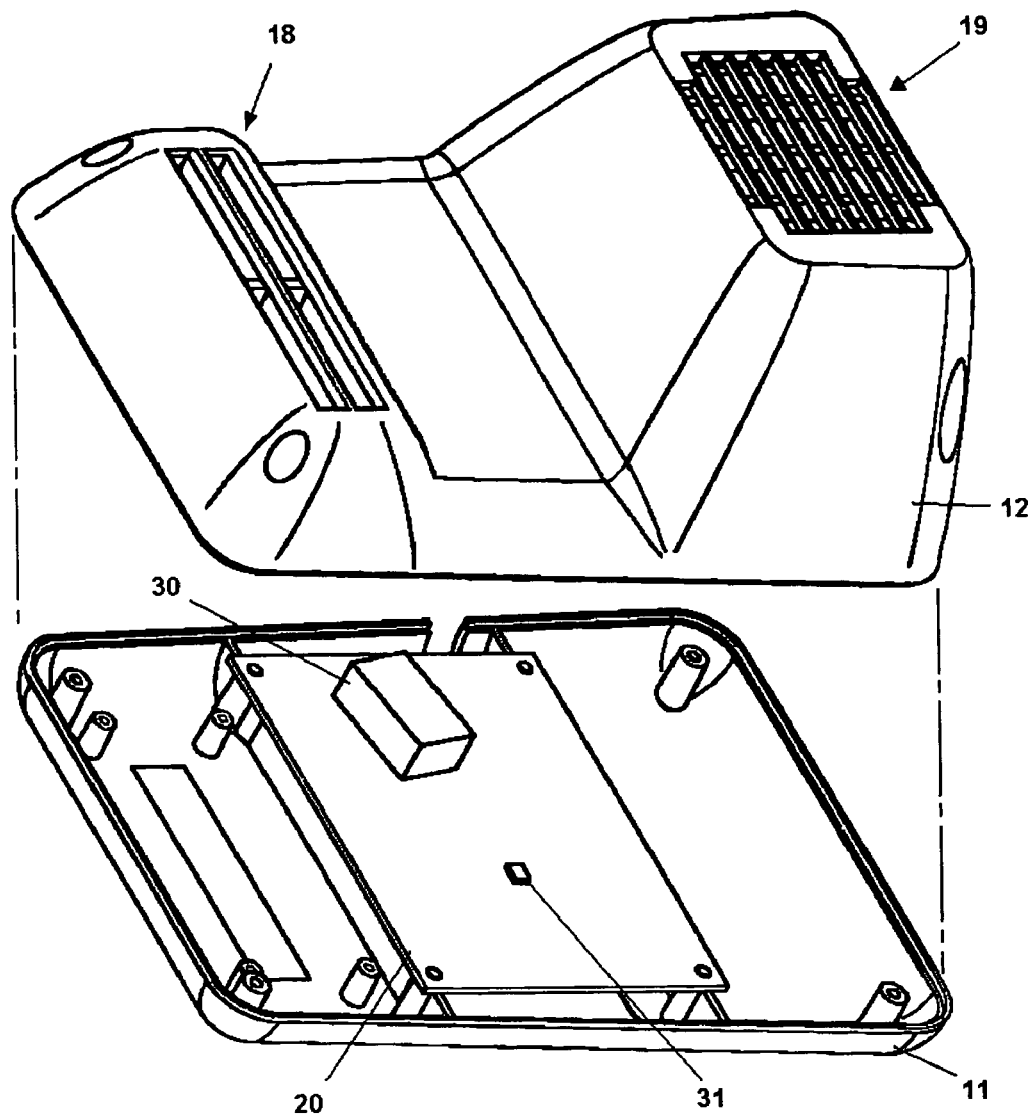
FIG. 2 is an exploded view of the apparatus of FIG. 1.

One embodiment of the invention is illustrated in FIG. 1 which shows a perspective view of particle sensor 10. FIG. 2 illustrates an exploded view of particle sensor 10 showing that the enclosure is made up of two pieces, an enclosure front 11 and an enclosure back 12 which are held together with screws. Also, a circuit board 20 is attached to the enclosure front 11. Circuit board 20 has attached to it photodetector 31 and light source 30. In this embodiment, the light source 30 is a collimated/focused laser beam. In this embodiment, the photodetector 31 is a Silicon PIN photodiode. In this embodiment, circuit board 20 contains circuitry familiar to those skilled in the art which will power the light source 30, convert the photodetector 31 output to electrical pulses, process those pulses to obtain size and count information, control the fan 50 (shown in FIG. 4), output data for display on the LCD 14 (shown in FIG. 1), monitor switch 13 inputs, and perform all other control and input/output functions for the particle sensor.

Figure 3:
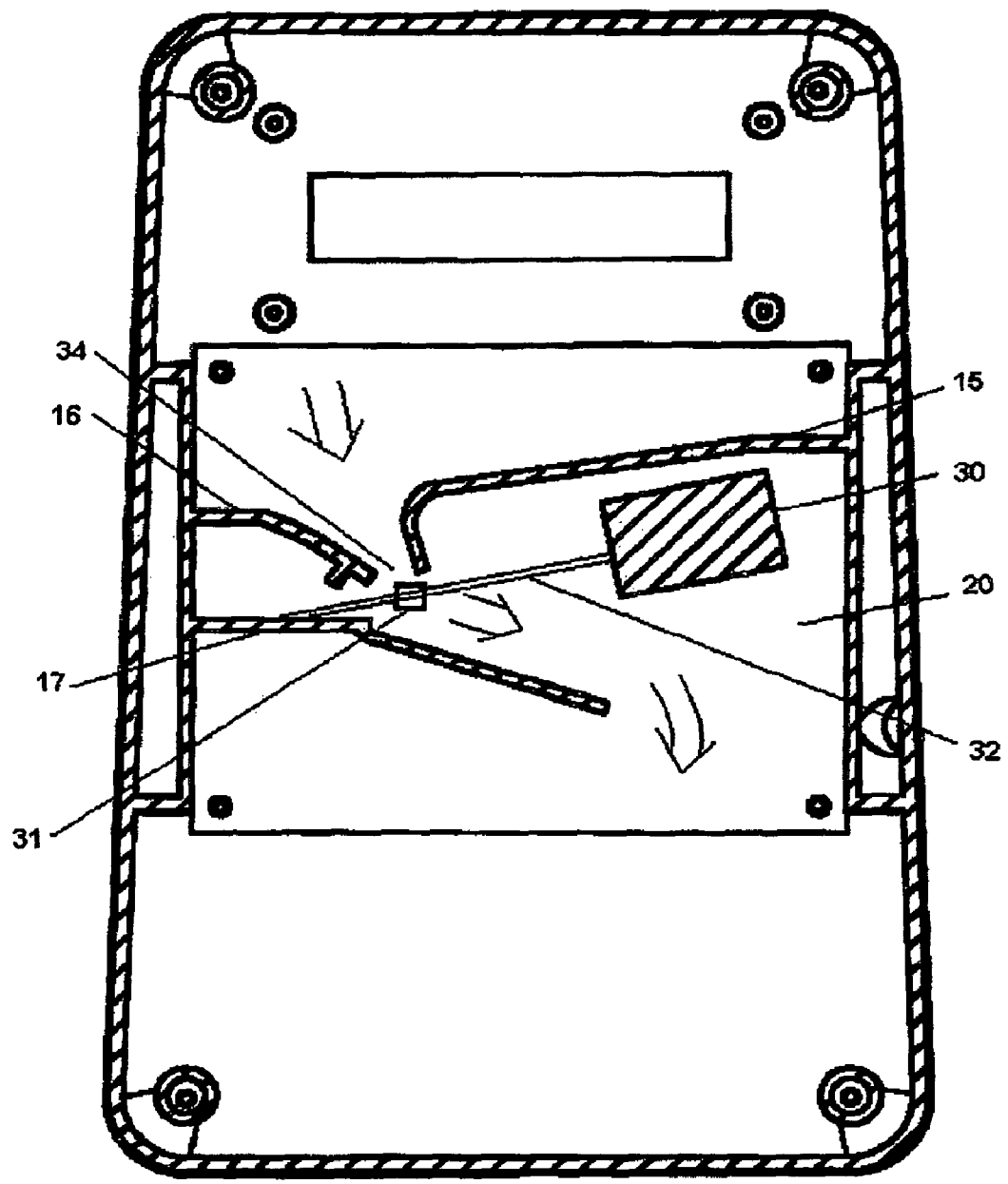
FIG. 3 is a cross section view of the apparatus of FIG. 1 taken through line 3-3 of FIG. 1.

FIG. 3 is a section view illustrating the positioning of the light source 30 and photodetector 31 relative to the baffles 15, 16, and 17. These baffles are molded into the rear enclosure 12 and serve to control stray light and direct air flow within the particle sensor (arrows show the direction of flow). The control of stray light, as is known to those skilled in the art, is important to reduce unwanted output from the photodetector 31. The baffles 15, 16, and 17 function to reduce stray light reaching the photodetector 31 from outside the particle sensor. In addition, baffles 16 and 17 reduce stray light from the light source 30 by forming what is known to those skilled in the art as a "light trap", "light stop", "beam dump", "beam stop", etc. FIG. 3 also illustrates the relationship between air flow passage 34. the beam of light 32, the photodetector 31, and the air flow. The air flow passage 34 is located upstream ("upsteam" is defined as the direction from which the air flow is coming) of the beam of light 32. Thus, the air first flows through the air flow passage 34 and then through the beam of light 32.

Figure 4:
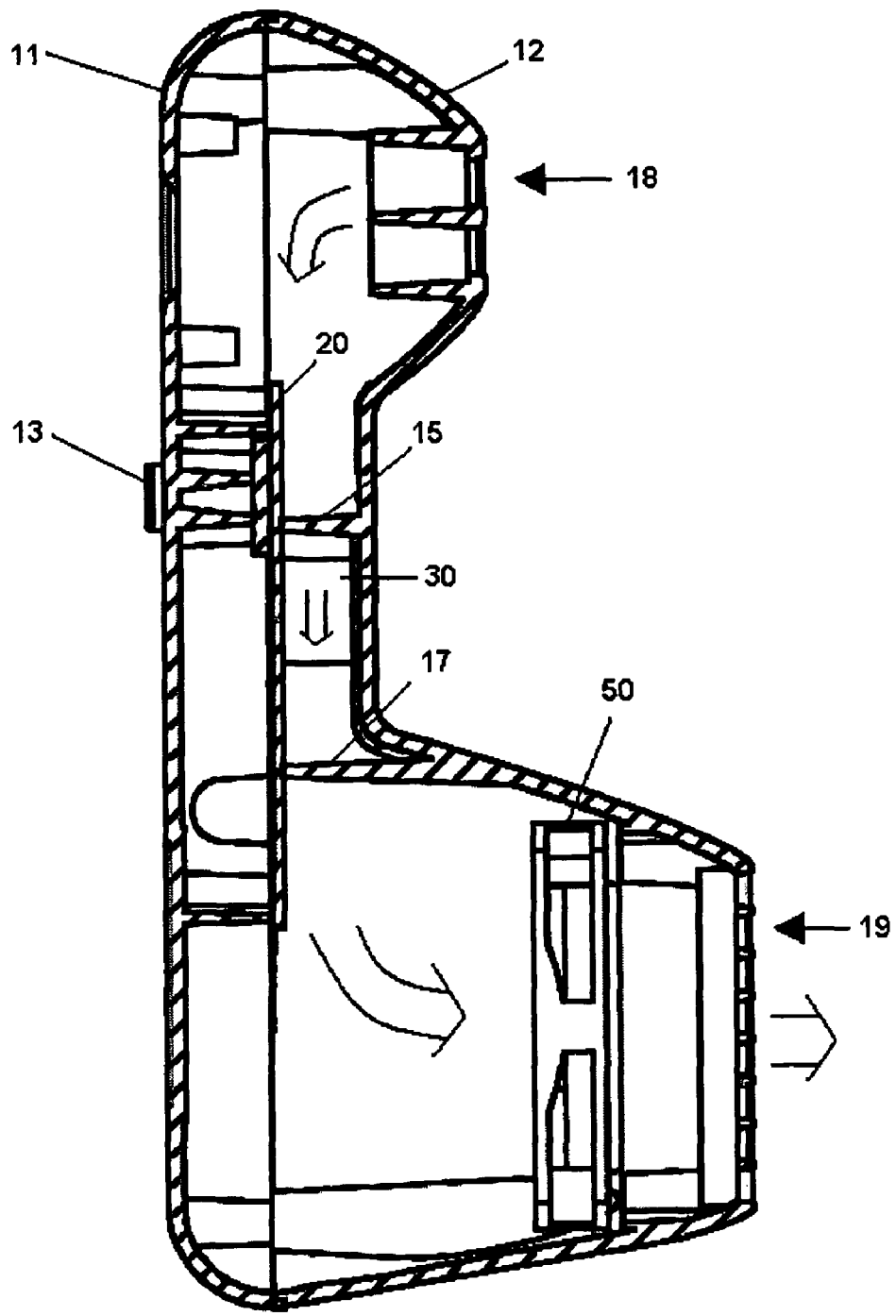
FIG. 4 is a cross section view of the apparatus of FIG. 1 taken through line 4-4 of FIG. 1.

FIG. 4 is a section view which further illustrates the air flow (shown by arrows) within the particle sensor. The air is drawn in through openings 18 at the top of the enclosure back 12 and exhausted out through openings 19 at the bottom of the enclosure back 12. In this embodiment, the air flow is created by axial fan 50. FIG. 4 also illustrates how the baffles 15, 16 (not shown), and 17 are part of the enclosure back 12 and contact the circuit board 20.

Figure 5:
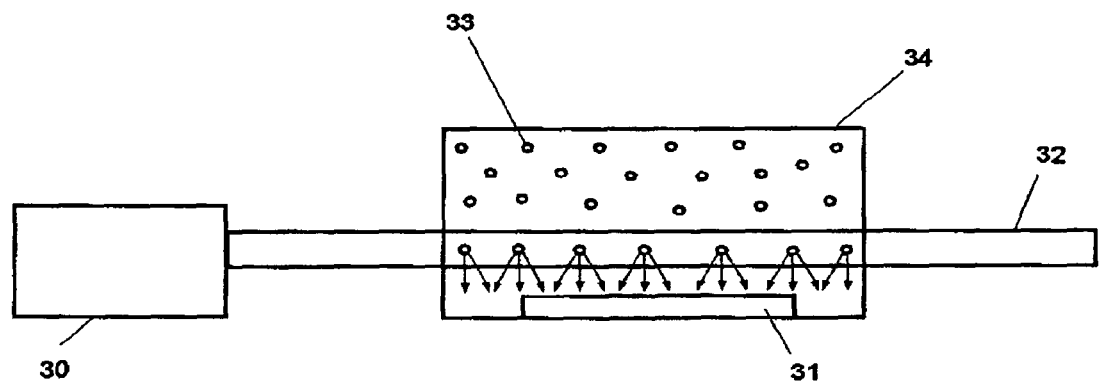
FIG. 5 is a diagrammatic view of the arrangement of the light source, light beam, photodetector, air flow opening and particle scattering.

FIG. 5 is a diagram (not to scale) which shows the positioning of the light source 30, the light beam 32, the photodetector 31, and the air flow passage 34. Also shown are particles 33 entrained in the air flow. In the diagram, the direction of air flow is into the page through air flow passage 34. The area of air flow passage 34 is greater than the area of the light beam 32 under the air flow passage 34 such that only a portion of the particles 33 passing through the particle sensor will traverse the light beam 32. By way of example, the cross sectional area of the flow passage 34 could be 75 square millimeters, the width of the beam of light 32 could be 0.5 millimeters, and the height of the beam above the photodetector could be 1.0 millimeters, although other geometries are possible. Again, by way of example, with the above geometry, many typical low cost axial fans (60 mm×60 mm) will produce less than 0.1 inches of pressure drop across the flow passage. As can be seen from the example dimensions and the small size of the axial fan, this embodiment permits a compact particle sensor to be constructed.

Continuing with FIG. 5, that portion of particles 33 which traverse the light beam 32 will scatter light as they pass through the beam. A portion of this scattered light is illustrated in FIG. 5 by arrows. As can be seen in FIG. 5, particles near the center of the photodetector 31 will scatter more light onto the photodetector 31 than particles near the edge of the photodetector. The pulse output of the photodetector for a given size particle will tend to be relatively uniform for particles near the center and will drop off rapidly for particles near or beyond the edge of the photodetector 31.

The rate at which air passing through the particle sensor is sampled for particles is the "effective flow rate" and is less than the actual flow rate of air through the air flow passage 34. To a first approximation, the effective flow rate is the flow of air through the light beam 32 directly over the photodetector 31. A more accurate calculation of the effective flow rate can be made by those skilled in the art by using Mie scattering theory, the light beam width, the geometry of the photodetector 31 relative to the light beam 32, the velocity of the air passing through the light beam, and the sensitivity of the photodetector as a function of the angle of incidence of the scattered light. Alternatively, those skilled in the art may determine the effective flow rate by 1) calibrating the count threshold of the photodetector output to its median response to uniform sized calibration particles, 2) measuring the count rate of the calibration particles, 3) determining the true concentration per unit volume of air of the calibration particles using a reference particle counter such as a Condensation Nucleus Counter, 4) calculating the effective flow rate by dividing the count rate by the true concentration and multiplying by 2. In this embodiment, the circuit board 20 contains a microprocessor and associated circuitry which, using techniques known to those skilled in the art, determines the count rate by monitoring the output of photodetector 31. This can be done using either analog, digital, or a mix of methods. The microprocessor then calculates the concentration of particles per unit volume by using the count rate and the effective flow rate. If the speed of the particles through the light beam 32 changes then the effective flow rate will change accordingly. The microprocessor can compensate for any change in flow rate by monitoring the pulse width of the photodetector response pulse and adjusting the value used for the effective flow rate when calculating the particle concentration.

In another embodiment, the particle sensor can control the axial fan or other flow generating device, using techniques known to those skilled in the art, to maintain a nominal pulse width and thus maintain a nominal effective flow rate.

Figure 6:
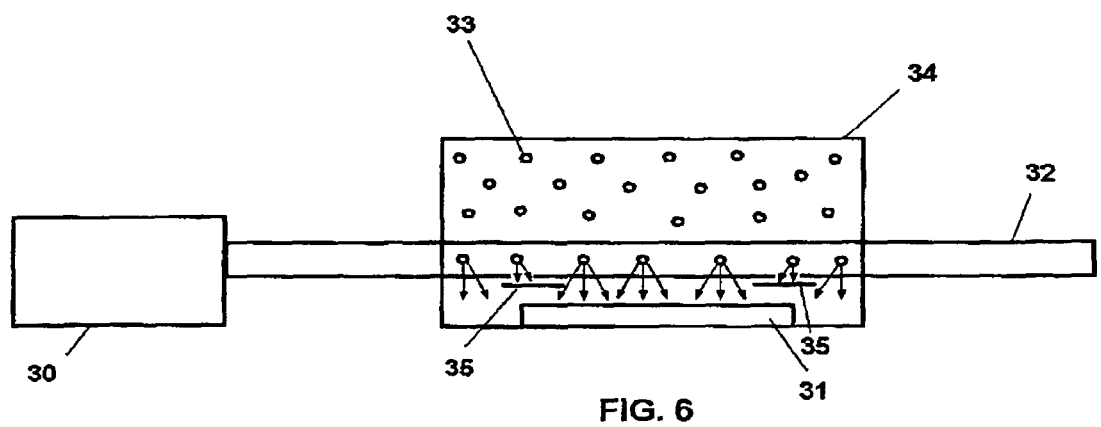
FIG. 6 is a diagrammatic view of the arrangement of the light source, light beam, photodetector, air flow opening, light baffle and particle scattering.

Another embodiment is shown in FIG. 6 which has a light baffle 35 between the light beam 32 and the photodetector 31. As known by those skilled in the art, the light baffle 35 improves the ability of the particle sensor to resolve particle size by blocking light from the more distant particles.

In another embodiment, a lens (not shown), with or without a light baffle, can be added between the light beam and the photodetector to further improve the particle size resolution.

Although the air flow passage is shown as rectangular in FIG. 5 and FIG. 6 and in a particular size relationship to the light beam 32 and the photodetector 31, other arrangements are possible including a non-rectangular shape for the air flow passage 34, an air flow passage 34 narrower than the photodetector 31, and other geometric configurations.

In an alternate embodiment, which is not described in the prior art, the photodetector output is digitally processed in a manner distinct from that described in U.S. Pat. No. 5,870, 190. In this new method the pulses will be digitized in a manner similar to that described in U.S. Pat. No. 5,870,190 but peak detection will not be used to size the particles.

Rather, the digitized pulses will essentially be integrated by summing the digital values obtained for each distinct pulse. This summation will be related to the total amount of light scattered by the particle and will be used to determine the particle size.

In an alternate embodiment, the photodetector output is digitally processed in a manner distinct from that described in U.S. Pat. No. 5,870,190. In this new method the pulses will be digitized in a manner similar to that described in U.S. Pat. No. 5,870,190 but peak detection will not be used to size the particles. Rather, the digitized output of the photodetector will be continuously monitored to check for a transition through the count threshold and if so a particle will be counted for the size corresponding to that threshold.

Although the description above contains many specificities, these should not be construed as limiting the scope of the embodiment but as merely providing illustrations of some of the presently preferred embodiments. Thus the scope of the embodiments should be determined by the appended claims and their legal equivalents, rather than by the examples given.

I claim:

1. A particle sensor using scattered light to detect and size particles entrained in air drawn from an environment into the particle sensor, said particle sensor comprising; a beam of light a photodetector in close proximity to said beam of light; an air flow passage located upstream of said beam of light; an air flow means for generating air flow through the particle sensor; wherein said beam of light intersects only a portion of said air flow.

2. The particle sensor of claim 1 wherein said air flow means includes an axial fan.

3. The particle sensor of claim 1 wherein the pressure drop across said air flow passage is less than 0.2 inches of H20.

4. The particle sensor of claim 1, further comprising a light baffle located between said beam of light and said photodetector.

5. The particle sensor of claim 4 wherein said air flow means includes an axial fan.

6. The particle sensor of claim 4 wherein the pressure drop across said air flow passage is less than 0.2 inches of H20.

7. A particle sensor using scattered light to detect and size particles entrained in air drawn from an environment into the particle sensor, said particle sensor comprising; a light source generating a beam of light; a photodetector in close proximity to said beam of light; an air flow passage located above upstream of said beam of light; an air flow means for generating air flow through the particle sensor; an electronic means for converting the output of said photodetector into pulses and analyzing those pulses for count and size information; wherein said beam of light intersects only a portion of said air flow.

8. The particle sensor of claim 7 wherein said electronic means calculates the effective flow rate of the particle sensor.

9. The particle sensor of claim 8 wherein said electronic means controls the flow means to regulate the effective flow rate.

10. The particle sensor of claim 7 wherein the entire particle senior is enclosed in a two piece molded plastic enclosure.

11. A method using scattered light for detecting and sizing particles entrained in an air flow, the method comprising steps of; generating a beam of light; directing said beam of light to pass above a photodetector in proximity to said photodetector; directing the air flow above the photodetector so that a portion of said air flow intersects said beam of light in proximity to said photodetector; analyzing the output of the photodetector to count and size particles in the air flow.

12. The method of claim 11 further comprising the step of calibrating the output of the photodetector by sampling calibration particles of known size.

13. The method of claim 12 further comprising the step of calculating the effective flow rate by comparing the count rate of a calibrated particle sensor with a reference particle counter.

14. The method of claim 11 further comprising the step of measuring a pulse width of the photodetector output and computing the effective flow rate of the particle sensor.

15. The method of claim 12 further comprising the step of measuring a pulse width of the photodetector output and computing the effective flow rate being sampled for particles.

16. The method of claim 13 further comprising the step of measuring a pulse width of the photodetector output and computing the effective flow rate being sampled for particles.

17. The method of claim 11 wherein the analysis of the photodetector output involves digitizing the photodetector output and summing the values within a pulse to obtain size information on the particle.

18. The method of claim 11 wherein the analysis of the photodetector output involves digitizing the photodetector output and monitoring the values for a transition through a count threshold.

* * * * *